(12) United States Patent
Chuh (10) Patent No.: US 6,953,048 B2
(45) Date of Patent: Oct. 11, 2005

(54) MODULAR SURFACE-MOUNT FLUID-FLOW SYSTEM

(75) Inventor: Yen Chuh, Irvine, CA (US)

(73) Assignee: Circle Seal Controls, Inc., Corona, CA (US)

( * ) Notice: Subject to any disclaimer, the term of this patent is extended or adjusted under 35 U.S.C. 154(b) by 12 days.

(21) Appl. No.: 09/949,255

(22) Filed: Sep. 7, 2001

(65) Prior Publication Data

US 2003/0047225 A1 Mar. 13, 2003

(51) Int. Cl.[7] .............................................. F16K 11/10
(52) U.S. Cl. ..................................... 137/269; 137/884
(58) Field of Search ................................ 137/269, 270, 137/271, 597, 884

(56) References Cited

U.S. PATENT DOCUMENTS

| | | | | |
|---|---|---|---|---|
| 5,488,925 A | * | 2/1996 | Kumada ...................... | 137/884 |
| 6,039,360 A | * | 3/2000 | Ohmi et al. .................. | 285/61 |
| 6,109,303 A | * | 8/2000 | Itafuji et al. ................ | 137/884 |
| 6,123,340 A | * | 9/2000 | Sprafka et al. ............. | 277/608 |
| 6,260,581 B1 | * | 7/2001 | Hollingshead .............. | 137/884 |
| 6,394,138 B1 | * | 5/2002 | Vu et al. ..................... | 137/884 |

OTHER PUBLICATIONS

"Modular Component Interface for Surface–Mount Fluid Distribution Components—Part 1: Elastomeric Seals", ANSI/ISA–76.00.002–2002 (American National Standard/ The Instrumentation, Systems, and Automation Society), Jun. 13, 2002.

* cited by examiner

Primary Examiner—John Fox
(74) Attorney, Agent, or Firm—McNees Wallace & Nurick LLC (57) ABSTRACT

A fluid-flow system includes a first plurality of substantially identical plate-like blocks. Each block has at least two fluid-flow through-passages extending between its front face and its back face. The blocks are connected to each other along their edge surfaces. A fluid component is affixed to the front face of each of the blocks, with its ports aligned and in fluid communication with the respective fluid-flow through-passages of the block to which it is affixed. A second plurality of fluid-flow block-interconnection tubes external to the blocks are affixed to the back face of a first block and to the back face of a second block. A first end of the fluid-flow block-interconnection tube is in fluid communication with one of the fluid-flow through-passages on the first block, and a second end of the fluid-flow block-interconnection tube is in fluid communication with one of the fluid-flow through-passages on the second block.

20 Claims, 4 Drawing Sheets

MODULAR SURFACE-MOUNT FLUID-FLOW SYSTEM

This invention relates to a surface-mount fluid-flow system and, more particularly, to a fluid sampling system.

BACKGROUND OF THE INVENTION

In continuous fluid-flow manufacturing industries such as the production of petrochemicals, a continuous flow of a fluid is periodically sampled and analyzed by an automated sampling-and-analysis system. The results of the analysis are used to control process operating parameters through a feedback control system. The present invention is concerned with the sampling and fluid control apparatus, rather than the analysis apparatus or the feedback control system.

In the sampling-and-analysis system, valves, regulators, gauges, flow indicators, and other fluid components are linked together to provide a sample of the process fluid flow to the analyzer and then to return the sample back to the process flow. The earliest sampling and analysis systems used conventional discrete fluid components linked by piping. These systems extract a relatively large volume of fluid in each sample, and the distances that the fluid must flow through the system are relatively large. Consequently, the sampling lag time is relatively long, which is undesirable from the standpoint of achieving good process control. These discrete-component systems have relatively high installed cost and maintenance cost.

The volume of fluid in the sample and the flow distance may be reduced by miniaturizing the system. In one approach, the fluid components are reduced in size as much as possible. The miniature fluid components are mounted to a surface of a support structure that provides both mechanical support for the fluid components and also mechanical and fluid interconnection between the fluid components.

This surface-mount fluid-flow system has the potential to reduce installed cost and maintenance cost for flow sampling, and a number of surface-mount systems have been proposed. However, the available systems have a number of shortcomings. Most installations are one-of-a-kind or require only a few of the same type of sampling-and-analysis systems, so that most installations are of a custom or semi-custom type. The available systems typically involve a large number of components, and/or expensive custom machining of components for each installation, and/or high assembly costs. The design procedures are also complex. Additionally, in some systems there is a potential for cross contamination between fluid streams within the apparatus, of a type that cannot be readily detected.

There is a need for an improved fluid-flow system that overcomes these problems. Such a fluid-flow system is needed for the sampling-and-analysis field, and for other fields as well. The present invention fulfills this need, and further provides related advantages.

SUMMARY OF THE INVENTION

The present invention provides an approach and apparatus for controlling fluid flows using a surface-mount technology. It uses a small number of different types of standardized elements to build complex systems, making the design, fabrication, assembly, and installation of fluid-flow systems relatively inexpensive. Maintenance costs are also relatively low. The present approach is therefore particularly well suited for sampling-and-analysis systems such as used in fluid process industries. The potential for undetected leakage and cross contamination is greatly reduced as compared with prior approaches.

In accordance with the invention, a fluid-flow system comprises a first stick. The first stick has a first plurality of substantially identical first-stick blocks. Each first-stick block is a plate having a front face, a back face, an edge face, and at least two fluid-flow through-passages extending between the front face and the back face. The first-stick blocks are connected to each other along their edge faces. The stick includes at least one fluid component affixed to the front face of each of the plurality of first-stick blocks. Each fluid component has ports thereon, with the ports of each fluid component being in fluid communication with the respective fluid-flow through-passages of the first-stick block to which it is affixed. There is a second plurality of first-stick fluid-flow block-interconnection tubes external to the first-stick blocks. Each first-stick fluid-flow block-interconnection tube is affixed to the back face of a first first-stick block with a first end of the fluid-flow block-interconnection tube in fluid communication with one of the fluid-flow through-passages on the first first-stick block, and also affixed to the back face of a second first-stick block with a second end of the fluid-flow block-interconnection tube in fluid communication with one of the fluid-flow through-passages on the second first-stick block. The fluid handled by the present approach may be a liquid or a gas.

In a preferred approach, the first-stick blocks are connected together in a linear array. The through-passages in each first-stick block all lie along a single line extending between two opposite ends of the first-stick block, parallel to the linear array where a linear array is used. The fluid-flow system may further include a mounting plate, and a set of mounting feet affixing the first-stick blocks to the mounting plate. There may be an adapter plate disposed between one of the fluid components and the respective block to which it is affixed. The adapter plate has fluid-flow passages therethrough providing fluid communication between one of the ports on the fluid component and one of the fluid-flow through passages of the respective block, and may also provide other capabilities such as a heater to heat the fluid passing therethrough.

The fluid-flow system also may include a second stick comprising a third plurality of substantially identical second-stick blocks, with the second-stick blocks being substantially identical to the first-stick blocks and connected to each other along their edge faces. There is at least one fluid component affixed to the front face of each of the plurality of second-stick blocks. Each fluid component has ports thereon, and the ports of each fluid component are in fluid communication with the respective fluid-flow through-passages of the second-stick block to which it is affixed. A fourth plurality of second-stick fluid-flow block-interconnection tubes are external to the second-stick blocks. Each second-stick fluid-flow block-interconnection tube is affixed to the back face of a first second-stick block with a first end of the fluid-flow block-interconnection tube in fluid communication with one of the fluid-flow through-passages on the first second-stick block, and also affixed to the back face of a second second-stick block with a second end of the fluid-flow block-interconnection tube in fluid communication with one of the fluid-flow through-passages on the second second-stick block. There is a fluid interconnection between the first stick and the second stick.

In a particularly preferred configuration, each block is a rectangular plate having a front face, a back face, a first pair of oppositely disposed edge faces, and a second pair of oppositely disposed edge faces. There are three fluid-flow through-passages in each block. The blocks are attached to each other in a linear array along the first pair of oppositely disposed edge faces by a first-stick-block attachment. The mounting plate comprises a set of rectangularly arranged mounting holes to which the first-stick mounting feet are affixed, and this array of mounting holes defines a rectilinear arrangement and positioning for the other components of the fluid-flow system. In this preferred structure, the block attachment between each block comprises a conformable step on each first-stick block of an attached pair of first-stick blocks, and an aligned attachment bore extending through the conformable steps, and a fastener extending through the attachment bore. Two different lengths of interconnection tube are required in this configuration, a first fluid-flow block-interconnection tube having a length sufficient to interconnect adjacent fluid-flow through passages, and a second fluid-flow block-interconnection tube having a length sufficient to interconnect two fluid-flow passages separated by another fluid-flow passage. The interconnection tubes are selected from these two lengths, and therefore only two different lengths of intra-stick interconnection tubes need be manufactured.

The present approach emphasizes good manufacturability and low cost of custom fluid-flow systems such as fluid-flow sampling systems. There is only one basic block type required, although modifications of the basic block type may be provided that do not have an end connector on one end and which are used as the end blocks of a stick. Each block has only holes and bores in its through-thickness direction, which are easily drilled with good precision. No holes or bores parallel to the front and back faces are used. There are only two basic lengths of intra-stick interconnection tubes required, so that only two such types of interconnection tubes need be fabricated and kept on hand. The rectilinear "pegboard" character of the mounting holes of the preferred mounting plate, which are aligned with comparable holes in the blocks, allows complex systems to be arranged and assembled rapidly and with no specialized fabrication procedures or tools applied. No custom machining is required for each stick. This structural simplicity translates to low labor requirements for the assembler and minimal chances of error.

Additionally, the present approach provides excellent technical capability. The general surface-mount architecture is used, and industry standards such as SP 76 are followed. Unlike many other surface-mount approaches, the interconnection tubes are open and visible. Leaks in the interconnection tubes and their attachments and seals are unlikely. However, if leaks do occur they are openly visible and readily repaired. If it is necessary to remove and replace or otherwise alter a block or a fluid-flow interconnection in the middle of a stick, these changes may be performed only with operations carried out at the block itself, and disassembly of the remainder of the system is not required. Further, there is no chance of cross contamination between two interconnection tubes and particularly no chance of cross contamination that goes undetected and therefore adversely influences the analytic results or the content of the fluid flows. The possibility of undetected leaks and the possibility of cross contamination are shortcomings with other architectures of fluid-flow systems.

The present approach therefore provides for a fluid-flow system that has low initial (capital) costs and low maintenance costs. The fluid-flow system is also highly reliable and, if repairs or changes are necessary, easy to alter. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
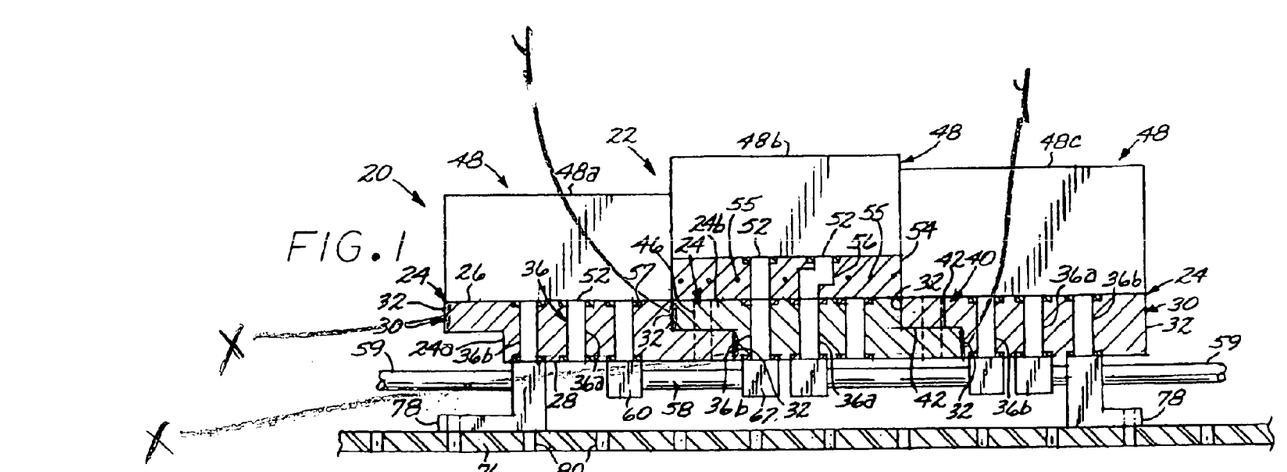
FIG. 1 is a schematic elevational view of a first stick of a fluid-flow system.
Figure 2:
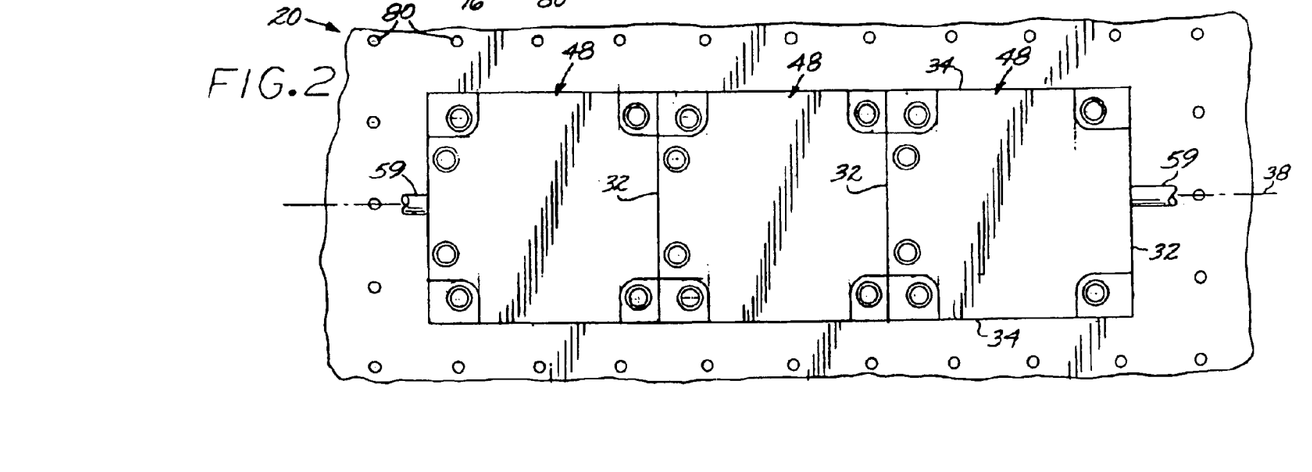
FIG. 2 is a schematic plan view of the first stick of FIG. 1.

FIGS. 1 and 2 depict a fluid-flow system 20 comprising a first stick 22. The term "stick" is a term of art applying to an interconnected array of "blocks" (usually linear in nature) and their fluid components and fluid-flow interconnections, which will be described subsequently. The stick 22 includes a first plurality of substantially identical first-stick blocks 24.

Figure 3:
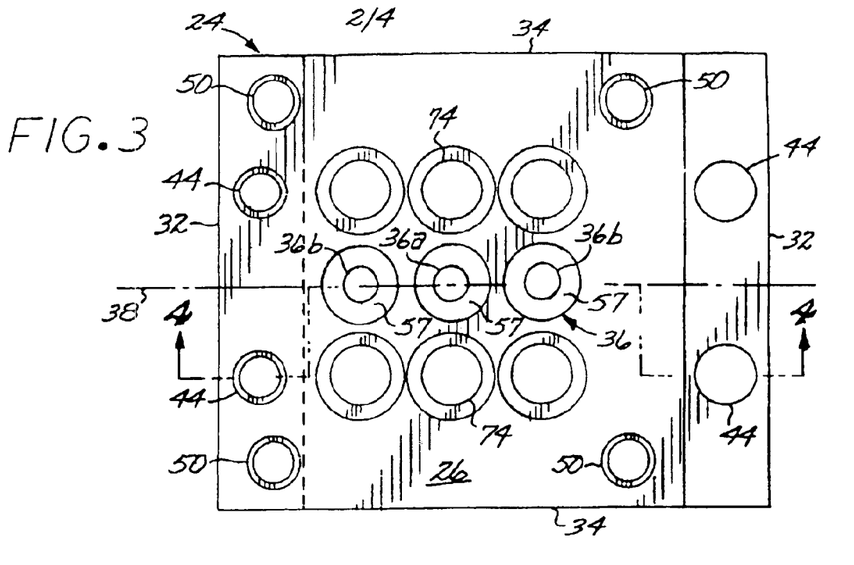
FIG. 3 is a plan view of a block used in the fluid flow system.
Figure 4:
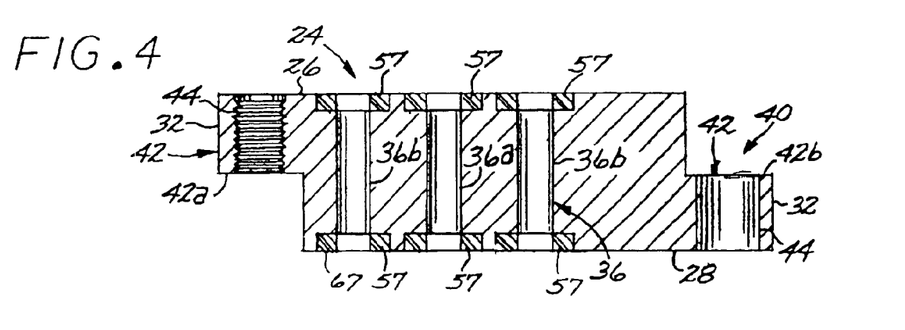
FIG. 4 is a sectional view of the block of FIG. 3, taken along line 4—4, illustrating a mid-stick block.
Figure 5:
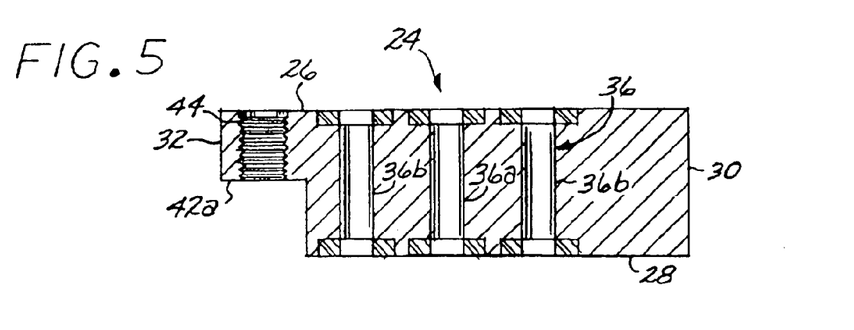
FIG. 5 is a sectional view like that of FIG. 3, except illustrating an end-stick block.

The structure of a block 24 is shown in FIGS. 3–5. Each block 24 has a front face 26, a back face 28, and an edge surface 30. Preferably, each block 24 is in the form of a rectangular plate as illustrated, so that there are first pair of oppositely disposed edge faces 32 and a second pair of oppositely disposed edge faces 34. There are at least two, and most preferably exactly three, fluid-flow through-passages 36 extending between the front face 26 and the back face 28. In the illustrated case of three fluid-flow through-passages 36, the three fluid-flow through-passages 36 include a center fluid-flow through passage 36a and two outer fluid-flow through-passages 36b. In this case, the three fluid-flow through-passages 36 lie along a stick axis 38 extending between the first pair of oppositely disposed edge faces 32 at a point midway between the second pair of oppositely disposed edge faces 34.

In the illustrated embodiment, the first-stick blocks 24 are attached to each other in a linear array oriented along the stick axis 38 at their first pairs of oppositely disposed edge faces 32 by a block attachment 40. The block attachment 40 preferably comprises a conformable step 42 on each block 24 of an attached pair of blocks 24. ("Conformable" means that the steps of two adjacent blocks 24 mechanically interface with each other so as to allow attachment therebetween.) Referring to FIG. 4, one of the steps 42a is on the side of the block 24 that includes the front face 26, and the other of the steps 42b is on the side of the block 24 that includes the back face 28. An aligned attachment bore 44 extends through the conformable steps 42a and 42b so that the portion of the attachment bore 44 within step 42a aligns with the portion of the attachment bore 44 that is within step 42b when two adjacent blocks 24 are affixed together as shown in FIG. 1. When the two adjacent blocks 24 are attached together, a fastener 46 such as a screw or bolt extends through the attachment bore 44 and joins the two adjacent blocks 24 together. For example, one end (here the end that is within the step 42a) of the attachment bore 44 may be threaded, and the fastener 46 is a bolt or screw that engages the threads from the other end (here the end that is within the step 42b) of the attachment bore 44. This type of block attachment 40 allows the attachment to be completed from either the front face 26 or the back face 28 during the assembly of blocks.

The block 24 is designed so that only one configuration of block 24 is required to build up a fluid-flow system 20. However, if only the type of block 24 shown in FIG. 4 is used, there is a step 42b extending out of one end of the stick 22, the right end in the view of FIG. 1. To square off the ends of the sticks 22, blocks 24 of the type shown in FIG. 5 are used at the appropriate ends of the sticks 22. FIG. 5 shows an end stick block with the step 42a at one end and the flat, squared-off surface 30 at the other end. However, the end block is otherwise identical to the mid-stick block shown in FIG. 4.

At least one, and typically exactly one, fluid component 48 is affixed to the front face 26 of each of the plurality of first-stick blocks 24. (This is the origin of the term "surface-mount" to describe the present architecture. All of the fluid components 48 are installed to the surface of the same front face 26 of the respective blocks 24.) The fluid components 48 include any component that is required in the fluid monitoring or control system. Examples of such fluid components 48 are valves of different types, flowmeters, filters, heaters, pressure transducers, pressure regulators, flow controllers, temperature sensors, instruments, analyzers, and the like. The structure and operation of the individual fluid components are known in the art and are not within the scope of the present invention.

The fluid components 48 are affixed to the respective blocks 24 by fasteners, preferably male-threaded fasteners, that engage the fluid components 48 and fluid-component attachment bores 50, which are preferably threaded with a female thread matching that of the fastener, extending downwardly from the front face 26 into the blocks 24. Four such attachment bores 50, arranged in a rectangular pattern, are illustrated in FIG. 3. The mechanical connections between the blocks 24 and the fluid components 48 at the fluid-component attachment bores 50 are preferably made to conform to the mounting provisions of SEMI 2787.1 and ISA Draft Specification SP76.00.03 (termed "SP76" in the industry) which set forth, among other things, the arrangement of ports, physical envelope constraints, mounting hole locations and sizes, and the like for surface-mounted fluid-control systems. A virtue of the present approach is that, if such specifications change in the future or other specifications are adopted, the block 24 and other mechanical components of the present approach may be readily adapted to such new specifications.

Each fluid component 48 has ports 52 thereon, through which fluid flows into or out of the fluid component. The ports 52 of each fluid component 48 are in fluid communication with one of the respective fluid-flow through-passages 36 of the block 24 to which it is affixed, as shown in FIG. 1. The fluid communication between the ports 52 and the fluid-flow through passage 36 may be direct, as shown for the leftmost and rightmost fluid components 48 in FIG. 1.

There may instead be an adapter plate 54 disposed between the fluid component 48 and the respective block 24 to which it is affixed, as seen for the center block 24 in FIG. 1. The adapter plate 54 has adapter-plate fluid-flow passages 56 therethrough providing fluid communication between one of the ports 52 on the fluid component 48 and one of the fluid-flow through passages 36 of the respective block 24. The adapter plate 54 thus allows a different port pattern of the fluid component 48 to be adapted to the standard pattern of the fluid-flow through passages 36 in the block 24. The adapter plate 54 may have other functions as well in performing as an auxiliary active device. Such auxiliary active device functions 55 include, for example, temperature measurement and/or control and flow direction and/or control. Examples of temperature measurement and/or control include a heater, a cooler, and a temperature measurement device such as a thermocouple within the adapter plate 54. Examples of flow direction and/or control include a check valve and an orifice in the flow channel within the adapter plate 54. In the adapter plate 54 of FIG. 1, to illustrate the auxiliary-active-device functions 55, an electrical resistance heater, represented by embedded insulated resistance wires, is built into the adapter plate 54 and powered by current from an external source (not shown).

The fluid connections between the ports 52 of the fluid component 48 and the fluid-flow through passages 36 are sealed with annular seals 57. The seals 57 preferably reside in recesses in the block 24 or the adapter plate 54, as appropriate. The seals 57 may be polymeric (for example, polytetrafluoroethylene), elastomeric (for example, a fluorocarbon such as Viton™ or Kalrez™ elastomer), or metallic, according to the type of fluid being processed. The polymeric or elastomeric seals are presently preferred.

The blocks 24 do not provide within themselves for the direct flow of fluid between the blocks, as for example a direct block-to-block fluid flow through sealed bores in the edge surfaces 30. Such fluid flow interconnection techniques result in an increased likelihood of undetected leakages and particularly cross contamination of fluid flows as a result of undetected leakages.

Figure 6:
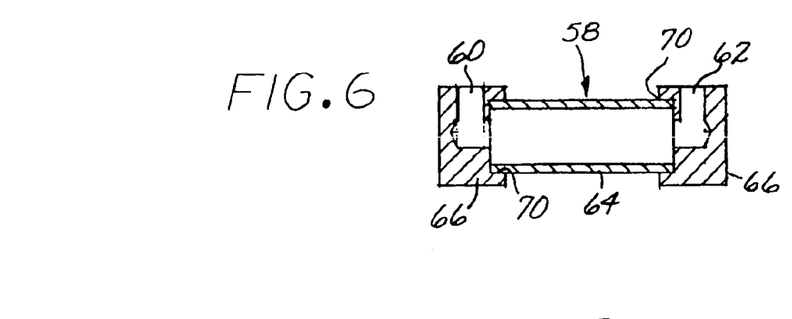
FIG. 6 is a schematic sectional view of a fluid-flow block interconnection tube.
Figure 7:
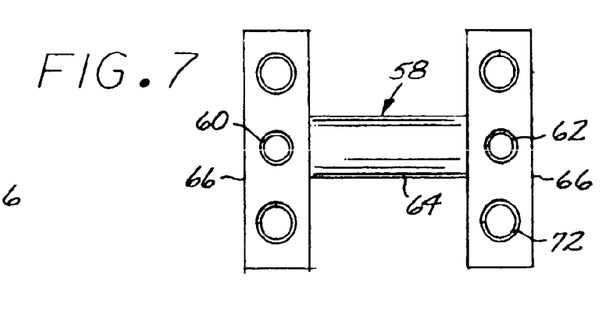
FIG. 7 is a schematic plan view of the fluid-flow block interconnection tube of FIG. 6.

Instead, the present approach provides for a second plurality of fluid-flow block-interconnection tubes 58 external to the blocks 24. The fluid-flow block-interconnection tube 58, which is shown in FIGS. 6–7, is affixed to the back face 28 of a first block, such as a block 24a in FIG. 1, with a first end 60 of the fluid-flow block-interconnection tube 58 in fluid communication with one of the fluid-flow through-passages 36 on the first block 24a. The fluid-flow block-interconnection tube 58 is also affixed to the back face 28 of a second block, such as a block 24b in FIG. 2, with a second end 62 of the fluid-flow block-interconnection tube 58 in fluid communication with one of the fluid-flow through-passages 36 on the second block 24b. Similarly, at least one interconnection tube 58 extends between the block 24b and the block 24c in FIG. 1.

As shown in FIGS. 4 and 6–7, each block interconnection tube 58 includes a tube 64 and a fitting 66 at each end 60 and 62. The tube 64 is brazed or welded to the fitting 66 at a joint 70. The back face 28 of the block 24 has seal recesses 67 that receives the annular seals 57 therein. The seal 57 seals the fluid-flow through passage 36 at its point of emergence from the back face 28 of the block 24 to the fitting 66. Each fitting 66 has two fitting attachment bores 72 therein, which align with corresponding fitting attachment bores 74 on the block 24. The fitting attachment bores 72 are preferably female threaded, so that a male-threaded fastener inserted from the front face 26 into the unthreaded fitting attachment bore 74 may be engaged to the threaded fitting attachment bores 72 to tighten the fitting 66 against the back face 28 of the block 24.

An important advantage of the present approach is that only two lengths of block interconnection tubes 58 are required for virtually all applications. One length is required to extend between two adjacent outer fluid-flow through-passages 36b in neighboring blocks 24, as shown for the block interconnection tube 58 connecting blocks 24a and 24b in FIG. 1. A second length is required to extend between a center fluid-flow through-passage 36a and the outer fluid-flow through-passage 36b of neighboring blocks 24, as shown for the block interconnection tube 58 connecting blocks 24b and 24c in FIG. 1. External interconnections may be made using these two lengths. The requirement to manufacture and stock only two lengths of block interconnection tubes 58, and to manufacture the stick 22 from only one type of block 24 (or two types, if the one end block is considered), is an important advantage of the present invention. Some other systems require over 100 components to accomplish a similar functionality. Reduced manufacturing complexity contributes greatly to reduced installed cost of the fluid-flow system.

External connections to and from the stick 22 are made with external interconnection tubes 59 that are similar to the block interconnection tubes 58, except that they are attached to the blocks 24 at one end and to some external connection at the other. The external interconnection tubes 59 may be cantilevered, as illustrated in FIG. 1, or affixed to the block 24 or to the mounting plate discussed next to provide them rigid support. This use of a tubular external interconnection tube 59 allows a great deal of flexibility in making external connections. Fluid connections between sticks are made with fluid-flow stick-to-stick interconnections discussed subsequently.

The fluid-flow system 20 further preferably includes a mounting plate 76 and a set of mounting feet 78 affixing the blocks 24 to the mounting plate 76. To facilitate the mounting and alignment, the mounting plate 76 desirably comprises a set of rectangularly arranged mounting holes 80 to which the mounting feet 78 are affixed. The fabrication of the fluid-flow system from the components is then accomplished by matching pre-existing holes and mounting structure. The mounting feet 78 are preferably in the form of L-shaped brackets whose lower end is fastened to the mounting holes 80 with fasteners such as screws or bolts, and whose upper end is affixed to the fitting attachment bore 74 either directly (as illustrated at the right-hand end of FIG. 1) or as part of one of the fittings of the interconnection tubes discussed subsequently in relation to FIGS. 6–7 and 9–10 (as illustrated at the left-hand end of FIG. 1).

Figure 8:
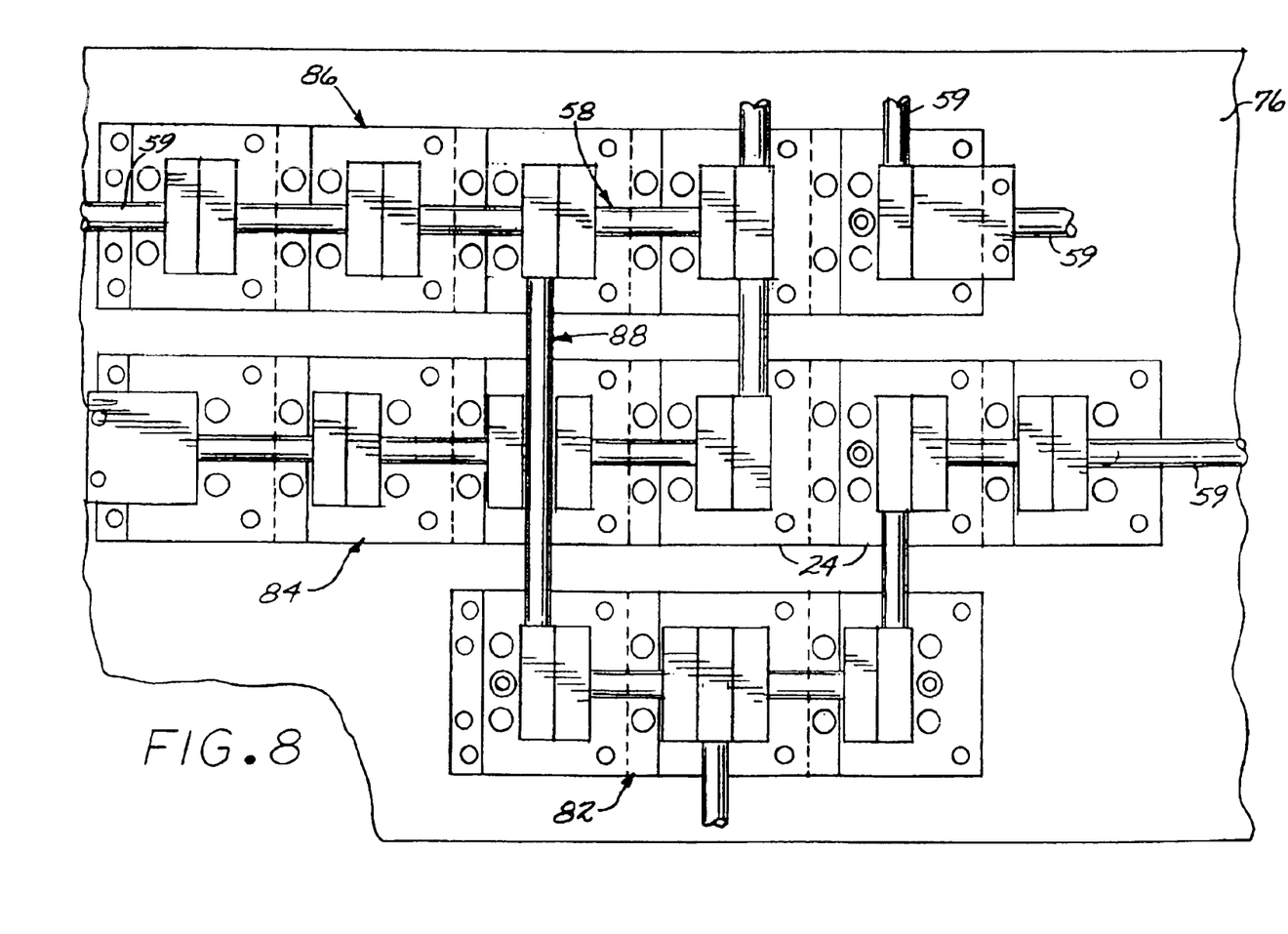
FIG. 8 is a schematic bottom view of a multi-stick fluid-flow system.

The stick 22 may be configured to perform any of a wide variety of functions, depending upon the selection of the fluid components 48 and the arrangements of the fluid-flow block interconnection tubes 58. In many types of fluid-flow systems 20, more-complex arrangements of the fluid-processing components are required. To achieve the higher complexity, multiple sticks 22 may be fabricated and mounted on the mounting plate 76 as illustrated in FIG. 8. In this case, three sticks 82, 84, and 86 are mounted to the mounting plate 76. The configuration of each stick 82, 84, and 86 is substantially as described earlier, except that the numbers of blocks, interconnections, and fluid components may be varied as necessary. In the illustration, stick 82 has 3 blocks, stick 84 has 6 blocks, and stick 86 has 5 blocks. Fluid interconnections between the sticks is made using a fluid-flow stick-to-stick interconnection tube 88 that extends between the sticks 82 and 84, or between the sticks 84 and 86, or between the sticks 82 and 86, as illustrated in FIG. 8. These fluid-flow stick-to-stick interconnection tubes 88 are oriented generally perpendicular to the fluid-flow block interconnection tubes 58. Alignment of the sticks and their interconnections is readily accomplished because of the rectilinear nature of the multi-stick structure achieved through the use of the mounting holes 80 in the mounting plate 76. The fluid-flow system of FIG. 8 is not intended to relate to any particular system, but instead is presented as an illustration of some of the possible types of fluid-flow interconnections within and between sticks, and external to the sticks.

Figure 9:
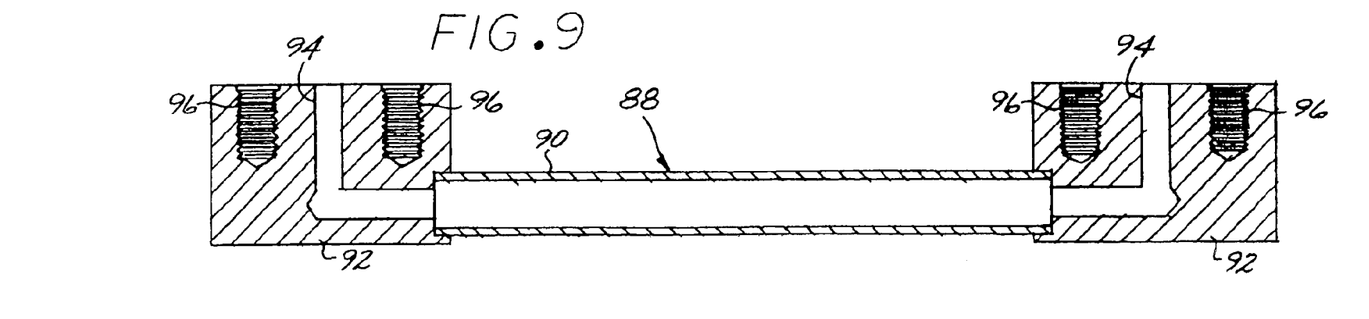
FIG. 9 is a schematic sectional view of a stick-to-stick interconnection tube.
Figure 10:
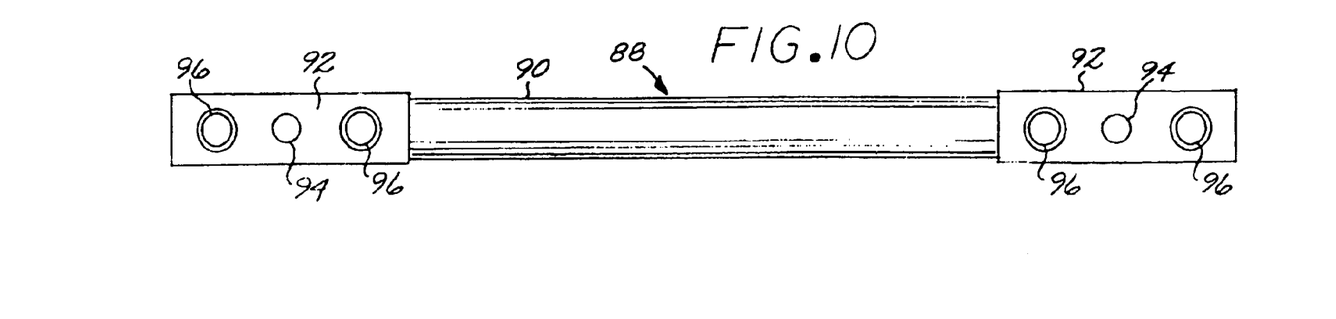
FIG. 10 is a schematic plan view of the stick-to-stick interconnection tube of FIG. 9.

The fluid–flow stick-to-stick interconnection 88, shown in detail in FIGS. 9–10, is similar in structure to the fluid-flow block interconnection 58. A tube 90 is affixed by welding or brazing at each end to a respective fitting 92. The fitting 92 has a flow passage 94 that is aligned with one of the fluid-flow through passages 36 of the block 24. Fitting attachment bores 96 align with the fitting attachment bores 74 of the block 24, and fasteners (not shown) inserted into the fitting-attachment bores 74 fasten the fitting 92 to the block 24. The seals 57 are used to seal the fittings 92 to the block 24 in the manner discussed earlier.

The components of the fluid-flow system 20 may be made of any operable material. Preferably, the block 24 and the interconnection tubes are made of type 316 stainless steel.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A fluid-flow system comprising a first stick having
   a first plurality of substantially identical first-stick blocks, each first-stick block being a plate having a front face, a back face, an edge face, and at least two fluid-flow through-passages extending between the front face and the back face, the first-stick blocks being attached to each other by a first-stick-block attachment including a fastener that extends through an attachment bore, the attachment bore extending through a first step and a second step when the first step and the second step are conformably positioned;
   at least one fluid component affixed to the front face of each of the plurality of first-stick blocks, each fluid component having ports thereon, the ports of each fluid component being in fluid communication with the respective fluid-flow through-passages of the first-stick block to which it is affixed; and
   a second plurality of first-stick fluid-flow block-interconnection tubes external to the first-stick blocks, each first-stick fluid-flow block-interconnection tube being affixed to the back face of a first first-stick block with a first end of the fluid-flow block-interconnection tube in fluid communication with one of the fluid-flow through-passages on the first first-stick block, and also affixed to the back face of a second first-stick block with a second end of the fluid-flow block-interconnection tube in fluid communication with one of the fluid-flow through-passages on the second first-stick block.

2. The fluid-flow system of claim 1, wherein the first-stick blocks are connected together in a linear array.

3. The fluid-flow system of claim 1, wherein the through-passages in each first-stick block all lie along a single line extending between two opposite ends of the first-stick block.

4. The fluid-flow system of claim 1, further including
a mounting plate, and
a set of mounting feet affixing the first-stick blocks to the mounting plate.

5. The fluid-flow system of claim 1, further including
a second stick comprising
   a third plurality of substantially identical second-stick blocks, the second-stick blocks being substantially identical to the first-stick blocks, the second-stick blocks being connected to each other along their edge faces,
   at least one fluid component affixed to the front face of each of the plurality of second-stick blocks, each fluid component having ports thereon, the ports of each fluid component being in fluid communication with the respective fluid-flow through-passages of the second-stick block to which it is affixed,
   a fourth plurality of second-stick fluid-flow block-interconnection tubes external to the second-stick blocks, each second-stick fluid-flow block-interconnection tube being affixed to the back face of a first second-stick block with a first end of the fluid-flow block-interconnection tube in fluid communication with one of the fluid-flow through-passages on the first second-stick block, and also affixed to the back face of a second second-stick block with a second end of the fluid-flow block-interconnection tube in fluid communication with one of the fluid-flow through-passages on the second second-stick block, and
a fluid-flow stick-to-stick interconnection tube extending between the first stick and the second stick.

6. The fluid-flow system of claim 1, further including
an adapter plate disposed between one of the fluid components and the respective block to which it is affixed, the adapter plate having fluid-flow passages therethrough providing fluid communication between one of the ports on the fluid component and one of the fluid-flow through passages of the respective block.

7. The fluid-flow system of claim 6, wherein the adapter plate comprises an auxiliary active device.

8. A fluid-flow system comprising
a first stick having
   a first plurality of substantially identical first-stick blocks, each first-stick block being a rectangular plate having a front face, a back face, a first pair of oppositely disposed edge faces, and a second pair of oppositely disposed edge faces, and three fluid-flow through-passages extending between the front face and the back face and lying on a stick axis extending between the first pair of oppositely disposed edge faces midway between the second pair of oppositely disposed edge faces, the first-stick blocks being attached to each other in a linear array by a first-stick-block attachment, wherein the first-stick-block attachment further comprises
      a step on each first-stick block of an attached pair of first-stick blocks;
      an attachment bore extending through the steps when the steps are conformably position; and
      a fastener extending through the attachment bore;
   one fluid component affixed to the front face of each of the plurality of first-stick blocks, each fluid component having ports thereon, the ports of each fluid component being in fluid communication with the respective fluid-flow through-passages of the first-stick block to which it is affixed;
   a second plurality of first-stick fluid-flow block-interconnection tubes external to the first-stick blocks, each first-stick fluid-flow block-interconnection tube being affixed to the back face of a first first-stick block with a first end of the fluid-flow block-interconnection tube in fluid communication with one of the fluid-flow through-passages on the first first-stick block, and also affixed to the back face of a second first-stick block with a second end of the fluid-flow block-interconnection tube in fluid communication with one of the fluid-flow through-passages on the second first-stick block;
a mounting plate; and
a set of first-stick mounting feet affixing the first-stick blocks to the mounting plate.

9. The fluid-flow system of claim 8, wherein the mounting plate comprises a set of rectangularly arranged mounting holes to which the first-stick mounting feet are affixed.

10. The fluid-flow system of claim 8, wherein each of the second plurality of fluid-flow block-interconnection tubes is selected from
   a first fluid-flow block-interconnection tube having a length sufficient to interconnect adjacent fluid-flow through passages, and
   a second fluid-flow block-interconnection tube having a length sufficient to interconnect two fluid-flow passages separated by another fluid-flow passage.

11. The fluid-flow system of claim 8, further including
an adapter plate disposed between one of the fluid components and the respective first-stick block to which it is affixed, the adapter plate having fluid-flow passages therethrough providing fluid communication between one of the ports on the fluid component and one of the fluid-flow through passages of the respective first-stick block.

12. The fluid-flow system of claim 1, wherein the adapter plate comprises an auxiliary active device.

13. The fluid-flow system of claim 8, further including
a second stick comprising
   a third plurality of substantially identical second-stick blocks, the second-stick blocks being substantially identical to the first-stick blocks, the second-stick blocks being connected to each other along their edge surfaces,
   at least one fluid component affixed to the front face of each of the plurality of second-stick blocks, each fluid component having ports thereon, the ports of each fluid component being in fluid communication with the respective fluid-flow through-passages of the second-stick block to which it is affixed, and
   a fourth plurality of second-stick fluid-flow block-interconnection tubes external to the second-stick blocks, each second-stick fluid-flow block-interconnection tube being affixed to the back face of a first second-stick block with a first end of the fluid-flow block-interconnection tube in fluid communication with one of the fluid-flow through-passages on the first second-stick block, and also affixed to the back face of a second second-stick block with a second end of the fluid-flow block-interconnection tube in fluid communication with one of the fluid-flow through-passages on the second second-stick block,
a fluid-flow stick-to-stick interconnection between the first stick and the second stick, and
a second set of second-stick mounting feet affixing the second-stick blocks to the mounting plate.

14. A fluid-flow system comprising
a first stick having
a first plurality of substantially identical first-stick blocks, each first-stick block being a rectangular plate having a front face, a back face, a first pair of oppositely disposed edge faces, and a second pair of oppositely disposed edge faces, and three fluid-flow through-passages extending between the front face and the back face and lying on a stick axis extending between the first pair of oppositely disposed edge faces midway between the second pair of oppositely disposed edge faces, the first-stick blocks being attached to each other in a linear array by a first-stick-block attachment wherein the first-stick-block attachment comprises
a step on each first-stick block of an attached pair of first-stick blocks,
an attachment bore extending through the steps when the steps are conformably positioned, and
a fastener extending through the attachment bore;
one fluid component affixed to the front face of each of the plurality of first-stick blocks, each fluid component having ports thereon, the ports of each fluid component being in fluid communication with the respective fluid-flow through-passages of the first-stick block to which it is affixed;
a second plurality of first-stick fluid-flow block-interconnection tubes external to the first-stick blocks, each first-stick fluid-flow block-interconnection tube being affixed to the back face of a first first-stick block with a first end of the fluid-flow block-interconnection tube in fluid communication with one of the fluid-flow through-passages on the first first-stick block, and also affixed to the back face of a second first-stick block with a second end of the fluid-flow block-interconnection tube in fluid communication with one of the fluid-flow through-passages on the second first-stick block; mounting plate comprising a set of rectangularly arranged mounting holes;
a set of first-stick mounting feet affixing the first-stick blocks to the mounting holes of the mounting plate;
a second stick comprising
a third plurality of substantially identical second-stick blocks, the second-stick blocks being substantially identical to the first-stick blocks, wherein pairs of the second-stick blocks are attached to each other by fasteners extending through attachment bores,
at least one fluid component affixed to the front face of each of the plurality of second-stick blocks, each fluid component having ports thereon, the ports of each fluid component being in fluid communication with the respective fluid-flow through-passages of the second-stick block to which it is affixed, and
a fourth plurality of second-stick fluid-flow block-interconnection tubes external to the second-stick blocks, each second-stick fluid-flow block-interconnection tube being affixed to the back face of a first second-stick block with a first end of the fluid-flow block-interconnection tube in fluid communication with one of the fluid-flow through-passages on the first second-stick block, and also affixed to the back face of a second second-stick block with a second end of the fluid-flow block-interconnection tube in fluid communication with one of the fluid-flow through-passages on the second second-stick block,
a fluid-flow stick-to-stick interconnection between the first stick and the second stick, and
a second set of second-stick mounting feet affixing the second-stick blocks to the mounting holes of the mounting plate.

15. The fluid-flow system of claim 14, wherein each of the second plurality of fluid-flow block-interconnection tubes is selected from
a first fluid-flow block-interconnection tube having a length sufficient to interconnect adjacent fluid-flow through passages, and
a second fluid-flow block-interconnection tube having a length sufficient to interconnect two fluid-flow passages separated by another fluid-flow passage.

16. The fluid-flow system of claim 14, further including
an adapter plate disposed between one of the fluid components and the respective first-stick block to which it is affixed, the adapter plate having fluid-flow passages therethrough providing fluid communication between one of the ports on the fluid component and one of the fluid-flow through passages of the respective first-stick block.

17. The fluid-flow system of claim 16, wherein the adapter plate comprises an auxiliary active device.

18. The fluid-flow system of claim 6, wherein the component has a port pattern that is different from a port pattern of the block, and the adapter plate provides a continuous port connection between the port pattern of the component and the port pattern of the block.

19. The fluid-flow system of claim 11, wherein the component has a port pattern that is different from a port pattern of the block, and the adapter plate provides a continuous port connection between the port pattern of the component and the port pattern of the block.

20. The fluid-flow system of claim 16, wherein the component has a port pattern that is different from a port pattern of the block, and the adapter plate provides a continuous port connection between the port pattern of the component and the port pattern of the block.

* * * * *

UNITED STATES PATENT AND TRADEMARK OFFICE
CERTIFICATE OF CORRECTION

PATENT NO.        : 6,953,048 B2                                    Page 1 of 1
APPLICATION NO. : 09/949255
DATED              : October 11, 2005
INVENTOR(S)       : Yen Chuh It is certified that error appears in the above-identified patent and that said Letters Patent is hereby corrected as shown below:

In column 9, line 10, claim 5 "connected to each other along" should be -- attached to each other at --.

In column 10, line 35, claim 12 "claim 1" should be -- claim 11 --.

In column 10, lines 43-44, claim 13 "connected to each other along their edge sufaces" should be -- attached to each other at the edge faces --.

Signed and Sealed this

Fourteenth Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 6,953,048 B2
APPLICATION NO. : 09/949255
DATED : October 11, 2005
INVENTOR(S) : Yen Chuh It is certified that error appears in the above-identified patent and that said Letters Patent is hereby corrected as shown below:

In column 9, line 10 claim 5, "connected to each other along" should be -- attached to each other at --.

In column 10, line 35 claim 12, "claim 1" should be -- claim 11 --.

In column 10, lines 43-44 claim 13, "connected to each other along their edge surfaces" should be -- attached to each other at the edge faces --.

Signed and Sealed this

Twenty-first Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 6,953,048 B2 Page 1 of 1
APPLICATION NO. : 09/949255
DATED : October 11, 2005
INVENTOR(S) : Yen Chuh It is certified that error appears in the above-identified patent and that said Letters Patent is hereby corrected as shown below:

This certificate vacates the Certificate of Correction issued October 21, 2008. The certificates is a duplicate of the Certificate of Correction issued October 14, 2008. All requested changes were included in the Certificate of Correction issued October 14, 2008.

Signed and Sealed this

Twenty-fifth Day of November, 2008

JON W. DUDAS
*Director of the United States Patent and Trademark Office*